US009867705B2

(12) United States Patent
Gettman (10) Patent No.: US 9,867,705 B2
(45) Date of Patent: Jan. 16, 2018

(54) PENILE SURGERY SYSTEMS AND METHODS (71) Applicant: Mayo Foundation for Medical Education and Research, Rochester, MN (US)

(72) Inventor: Matthew T. Gettman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 315 days.

(21) Appl. No.: 14/652,896

(22) PCT Filed: Dec. 17, 2013

(86) PCT No.: PCT/US2013/075601
§ 371 (c)(1),
(2) Date: Jun. 17, 2015

(87) PCT Pub. No.: WO2014/099873
PCT Pub. Date: Jun. 26, 2014

(65) Prior Publication Data
US 2015/0335431 A1 Nov. 26, 2015

Related U.S. Application Data (60) Provisional application No. 61/738,692, filed on Dec. 18, 2012.

(51) Int. Cl.
*A61F 2/26* (2006.01)
*A61G 13/12* (2006.01)
(Continued)

(52) U.S. Cl.
CPC ........ *A61F 2/26* (2013.01); *A61B 17/320016* (2013.01); *A61B 90/37* (2016.02);
(Continued)

(58) Field of Classification Search
CPC ........................................................ A61F 2/26
(Continued)

(56) References Cited

U.S. PATENT DOCUMENTS 4,653,485 A * 3/1987 Fishell ............... A61F 2/26
600/40
2003/0125724 A1 7/2003 Long
(Continued)

FOREIGN PATENT DOCUMENTS

WO WO2005062696 A2 7/2005

OTHER PUBLICATIONS

"The DigiFuseTM Cannulated Implant System," www.metasurg.com [online]. Retrieved from the Internet: <URL: http://www.metasurg.com/downloads/Metasurg_DigiFuse_New2012_sngls.pdf>, 4 pages, 2012.
(Continued)

*Primary Examiner* — Samuel Gilbert
(74) *Attorney, Agent, or Firm* — Fish & Richardson P.C.

(57) ABSTRACT

This document provides methods and systems for penile surgery. For example, methods and systems for implanting penile prostheses to treat ED are provided. The methods and systems provided herein can include scaffolding for penile stabilization, imaging techniques to facilitate accurate tunneling of the corpora cavernosa, corporal fibrotic tissue removal devices, and penile prostheses configured for over-the-wire installation.

16 Claims, 4 Drawing Sheets (51) Int. Cl.
  A61B 17/32    (2006.01)
  A61B 18/00    (2006.01)
  A61B 18/12    (2006.01)
  A61B 90/00    (2016.01)

(52) U.S. Cl.
  CPC .. *A61G 13/1205* (2013.01); *A61B 17/320036* (2013.01); *A61B 2018/0022* (2013.01); *A61B 2018/126* (2013.01); *A61B 2090/376* (2016.02)

(58) Field of Classification Search
  USPC .................................................... 600/38–41
  See application file for complete search history.

(56) References Cited

U.S. PATENT DOCUMENTS

2010/0010530 A1    1/2010    Rhee
2011/0071344 A1    3/2011    Morningstar et al.

OTHER PUBLICATIONS

"Хирургическое лечение эректильной дисфункции," [Surgical treatment of erectile dysfunction] medbe.ur [online] 2011, Retrieved from the Internet: <URL: http://medbe.ru/materials/andrologiya/khirurgicheskoe-lechenie-erektilnoy-disfunktsii/>, [English machine translation], 36 pages.
Chen et al., "Bioengineered corporal tissue for structural and functional restoration of the penis," Proc Natl Acad Sci U S A., 107(8)3346-3350, Epub Nov. 13, 2009.
Kucukdurmaz and Kadioglu, "Surgical Treatment of Erectile Dysfunction," Erectile Dysfunction—Disease-Associated Mechanisms and Novel Insights into Therapy, Ch. 9, pp. 161-184, Feb. 29, 2012.
Savich et al., "Эктопическая установка резервуара при имплантации трехкомпонентного пенильного протеза" [Ectopic installation vessel when implanted penile prosthesis three] UroWeb.ru [online] Jul. 16, 2009 [retrieved on Oct. 28, 2015]. Retrieved from the Internet: <URL: http://uroweb.ru/print/2903> [English machine translation], 4 pages.
Shaeer and Shaeer, "Penile prosthesis surgery for the fibrotic penis," Current Sexual Health Reports, 5:179-181, 2008.
Shaeer, "Implantation of penile prosthesis in cases of corporeal fibrosis: modified Shaeer's excavation technique," J Sex Med., 5(10):2470-2476, Epub Jul. 1, 2008.
Shaeer, "Penoscopy: optical corporotomy and resection for prosthesis implantation in cases of penile fibrosis, Shaeer's technique," J Sex Med., 4(5):1214-1217, Sep. 2007.
Sievert et al., "Tissue engineering for the lower urinary tract: a review of a state of the art approach," Eur Urol., 52(6):1580-1589, Epub Sep. 4, 2007.
Wolf, "Urethrotomes," 2011, [retrieved on Oct. 28, 2015]. Retrieved from the Internet: <URL: http://medimpex.su/sites/default/files/prices/Price_Urethrotomes.pdf> 10 pages.
International Search Report and Written Opinion for PCT/US2013/075601, dated Mar. 27, 2014, 10 pages.
International Preliminary Report on Patentability for PCT/US2013/075601, dated Jul. 2, 2015, 8 pages.

* cited by examiner

PENILE SURGERY SYSTEMS AND METHODS

CROSS-REFERENCE TO RELATED APPLICATIONS

This application is a National Stage application under 35 U.S.C. §371 of International Application No. PCT/US2013/075601, having an International Filing Date of Dec. 17, 2013, which claims the benefit of U.S. Provisional Application Ser. No. 61/738,692, filed Dec. 18, 2012. The disclosure of the prior application is considered part of (and is incorporated by reference in) the disclosure of this application.

BACKGROUND

1. Technical Field

This document relates to systems and methods for performing penile surgery. For example, this document relates to methods and systems for implanting penile prostheses to treat erectile dysfunction. The document also relates to methods, modalities, and systems for other implantable treatments for erectile dysfunction.

2. Background Information

Erectile dysfunction (ED) is estimated to affect 20-30% of men aged between 40-80 years. Surgical treatment, especially penile prosthesis implantation, is the standard of care in cases of medication-resistant ED. Potential adverse effects associated with certain current techniques for penile prosthesis implantation can include rupture of the tunica albuginea, neurovascular injury, and urethral injury. Preoperative presence of fibrotic tissue in the corpora cavernosa is an additional risk factor that can contribute to sub-optimal outcomes for penile prosthesis implantation using current techniques. While penile prostheses represent the standard of care for medication-resistant ED, another consequence of implantation is that the corpus cavernosum is rendered permanently non-functional in regards to other medical treatments.

SUMMARY

This document provides methods and systems for performing penile surgery. For example, this document provides methods and systems for implanting penile prostheses to treat ED. The document also provides methods, modalities, and systems for other implantable treatments for erectile dysfunction.

In general, one aspect of this document features methods for implanting a penile prosthesis. A method comprises inserting a needle into a corpora cavernosa of a male human; injecting, via said needle, contrast dye into said corpora cavernosa; observing, using radiography, a position of said needle in relation to said corpora cavernosa; directing, in response to said observing, said needle to a desired position in relation to said corpora cavernosa; inserting a guidewire through a lumen of said needle; removing said needle from said corpora cavernosa; inserting a dilator into said corpora cavernosa; dilating said corpora cavernosa; inserting a penile implant into said corpora cavernosa; and removing said guidewire.

These and other embodiments may each optionally include one or more of the following features. For instance, the method may comprise installing a penile stabilization device to a penis of said male human. The method may comprise removing fibrotic tissue from said corpora cavernosa. The method may comprise inserting an anterior penile implant into an anterior portion of said corpora cavernosa; inserting a posterior penile implant into a posterior portion of said corpora cavernosa; and coupling said anterior penile implant to said posterior penile implant, wherein said coupling is performed with said anterior penile implant being at least partially within said anterior portion of said corpora cavernosa and with said posterior penile implant being at least partially within said posterior portion of said corpora cavernosa.

In general, another aspect of this document features systems for implanting a penile prosthesis. A system comprises a needle with a lumen, wherein said needle is configured to inject a contrast dye into a corpora cavernosa; a radiography system configured to display an image of said contrast dye within said corpora cavernosa; a guidewire configured to be inserted through said lumen of said needle and configured to be inserted into said corpora cavernosa; and a dilator configured to be installed over said guidewire into said corpora cavernosa, and configured to dilate said corpora cavernosa; and a penile prosthesis.

These and other embodiments may each optionally include one or more of the following features. For instance, the system may comprise a penile stabilization device. The system may comprise a device configured for severing fibrotic tissue from within said corpora cavernosa. The system may be configured for severing fibrotic tissue comprises a blade configured to shear said fibrotic tissue, wherein said device comprises a lumen configured for installation over said guidewire. The system may be configured for severing fibrotic tissue comprises a balloon with a bi-polar electro-cautery portion on a distal tip of said balloon, wherein said balloon is configured for installation over said guidewire.

In general, another aspect of this document features penile stabilization devices. A penile stabilization device comprises: a urethral protector, comprising an elongate element configured to be inserted into a urethra of a penis, an outer portion coupled to said elongate element and configured to be attached to an outer surface of said penis; one or more arm members, comprising a first end configured to be coupled to said outer portion of said urethral protector and a second end configured to be coupled to a base; one or more clamping joints, wherein said clamping joints are configured to switch between a loosened configuration and a tightened configuration, wherein in said loosened configuration said penile stabilization device is flexibly movable, and wherein in said tightened configuration said penile stabilization device is rigidly fixed in a position.

In general, another aspect of this document features penile prostheses systems. A penile prosthesis system comprises a guidewire; and an inflatable penile prosthesis comprising a chamber and a central lumen, wherein the central lumen is arranged to releasably receive the guidewire, and wherein the guidewire is capable of guiding the inflatable prosthesis during implantation into a penis. Another penile prosthesis system comprises a guidewire; and a penile prosthesis comprising a chamber and a central lumen, wherein the central lumen is arranged to releasably receive the guidewire, and wherein the guidewire is capable of guiding the inflatable prosthesis during implantation into a penis.

In general, another aspect of this document features methods for treating erectile dysfunction. A method for treating erectile dysfunction comprises: inserting a needle into a corpora cavernosa of a male human; injecting, via said needle, contrast dye into said corpora cavernosa; observing, using radiography, a position of said needle in relation to said corpora cavernosa; directing, in response to said observing, said needle to a desired position in relation to said corpora cavernosa; and injecting tissue engineered materials or growth factors into said copora cavernosa.

In general, another aspect of this document features penile prostheses devices. An inflatable penile prosthesis device comprises a chamber and a central lumen, wherein the central lumen is arranged to releasably receive the guidewire, and wherein the guidewire is capable of guiding the inflatable penile prosthesis during implantation into a penis. Another penile prosthesis device comprises a plurality of mini-rods, wherein said mini-rods are configured to be implanted into a penis and arranged in a geometric fashion to function collectively as a non-inflatable penile prosthesis.

Particular embodiments of the subject matter described in this document can be implemented to realize one or more of the following advantages. In some embodiments, a scaffolding system can be used to stabilize penal anatomy to provide positional consistency, predictability, and stability for better surgical outcomes. A radiographically-guided corpora cavernosa tunneling technique can provide increased surgical accuracy and enhanced patient safety during the corpora cavernosa dilation process. Fibrotic tissue removal devices can improve penile prosthesis implantation outcomes in cases of corporal fibrosis. A novel penile prosthesis design that includes a central insertion channel enabling the operator to place the prosthesis over a guidewire is provided herein. In addition, the use of image-guided access tracts in the corpora can provide a means of delivering other types of prostheses and treatments for ED. For example, the image-guided techniques described herein can be used to deliver tissue engineered cells and growth factors to treat erectile dysfunction.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides methods and systems for penile surgery. For example, this document provides methods and systems for implanting penile prostheses to treat ED. The methods and systems provided herein include scaffolding for penile stabilization, an imaging technique to facilitate accurate tunneling of the corpora cavernosa, and corporal fibrotic tissue removal devices.

In some cases, a penile scaffolding system provided herein can be used to stabilize the anatomy during surgery. In some cases, a penile scaffolding system can include a sterile insertable urethral protector device. The urethral protector device can include an outer flange portion and an elongate shank portion. The elongate shank portion can be insertable in the male urethra. In some cases, the outer flange portion can be releasably coupled to the penis by clamping to the skin, or the periphery of the penis below the glans. With the urethral protector device so engaged with the penis, the urethral protector device can be used effectively to control the position of the penis as desired for a surgical procedure.

In some cases, a penile scaffolding system provided herein can include one or more rigid clamping arms. The clamping arms can be used to couple with the outer flange portion of the urethral protector device, and to couple with a stable base such as an operating table. The clamping arms can be flexibly maneuverable during set-up, and then locked in a fixed position for surgery. In that fashion, the penile scaffolding system provided herein can be used to stabilize the anatomy for improved positional consistency, predictability, and stability.

In some cases, a method provided herein using an imaging system can be used to facilitate accurate tunneling of the corpora cavernosa. In some cases, a physician can use a needle to inject a contrast dye into the corpora cavernosa. The location of the needle in relation to the corpora cavernosa can be ascertained by observing the contrast dye using, for example, a fluoroscopic imaging system. As the physician is observing the image, the physician can advance the needle while continuing to inject additional contrast dye. Using this imaging technique, the physician can progress the needle through the corpora cavernosa approximately on the central axis of the corpora cavernosa, or in any position as desired.

In some cases, corporal fibrotic tissue removal devices provided herein can be used to remove fibrotic corporal tissue. In some cases, an over-the-wire incision device can be used to remove fibrotic corporal tissue. In some cases, an expandable balloon cautery device can be used to remove fibrotic corporal tissue.

Figure 1:
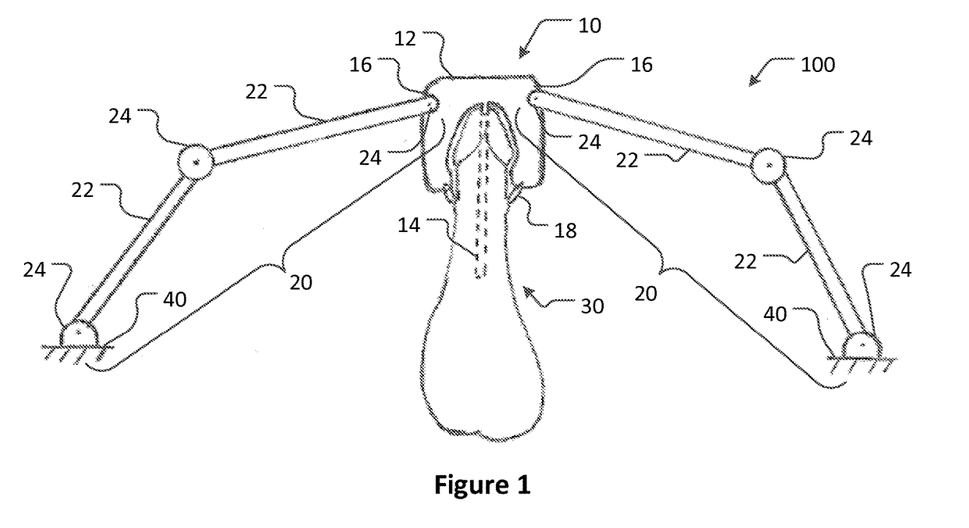
FIG. 1 is a schematic diagram of a penile scaffold system in accordance with some embodiments provided herein.

With reference to FIG. 1, a penile scaffold system 100 can include an insertable urethral protector device 10 and one or more rigid clamping arms 20. Penile scaffold system 100 can be used to stabilize the anatomy of a patient during penile surgery and to perform a certain amount of traction of a penis 30.

Insertable urethral protector device 10 can comprise a biocompatible sterile material. In some cases, insertable urethral protector device 10 can comprise a polymeric material such as polytetrafluoroethylene, polyethylene, polyvinylchloride, polycarbonate, and the like. In some cases, insertable urethral protector device 10 can comprise a metallic material such as stainless steel. In some cases, insertable urethral protector device 10 can be a disposable single-use device. In some cases, insertable urethral protector device 10 can be a reusable device, in which case it can be resterilized, for example, in an autoclave.

Insertable urethral protector device 10 can include an outer flange portion 12 and an elongate shank portion 14. In some cases, outer flange portion 12 and elongate shank portion 14 can comprise a single piece of material. For example, in some cases, outer flange portion 12 and elongate shank portion 14 can be injection molded as a single polymeric component. In some cases, outer flange portion 12 and elongate shank portion 14 can be made as separate parts that are subsequently joined together. For example, in some cases, outer flange portion 12 and elongate shank portion 14 can be glued, welded, mechanically fastened together, or otherwise conjoined using any suitable technique.

Outer flange portion 12 can be on the exterior of penis 30, while elongate shank portion 14 can be substantially within the interior of penis 30. In some cases, elongate shank portion 14 can be inserted in the urethra of penis 30. Outer flange portion 12 can be configured with one or more clamp locations 16 where rigid clamping arms 20 can be coupled. In some cases, outer flange portion 12 can be substantially planar with a thickness of about two to about 10 mm, or about five to about 15 mm. In some cases, outer flange portion 12 can be substantially cylindrical, or any other suitable shape. Outer flange portion 12 can be configured with one or more penal attachment devices 18. Penal attachment devices 18 releasably couple outer flange portion 12 to penis 30. In some cases, penal attachment devices 18 can be clamps that secure to a portion of skin of penis 30. In some cases, penal attachment devices 18 can be clamps that secure to a periphery or portion of a periphery of penis 30. In some cases, penal attachment devices 18 are sutures. For example, penal attachment devices 18 can be sutures that tie outer flange portion 12 to the skin of penis 30.

Elongate shank portion 14 can have a cylindrical or any other suitably shaped cross-section. Elongate shank portion 14 can have a diameter that approximates the diameter of the urethra, and can be available in a range of sizes. For example, in some cases, elongate shank portion 14 can have a diameter of about two to about 10 mm, about three to about eight mm, or about four to about seven mm. Elongate shank portion 14 can have an axially length that correlates to the length of the exterior portion of penis 30, and can be available in a range of sizes. For example, in some cases, elongate shank portion 14 can have a length of about 70 to about 150 mm, about 80 to about 140 mm, about 90 to about 130 mm, or about 100 to about 120. In some cases, the length of elongate shank portion 14 can be customizable by the physician at the time of the surgery.

Rigid clamping arms 20 can include one or more arms members 22 and one or more adjustable clamping joints 24. At least one arm member 22 can be clamped to outer flange portion 12 of insertable urethral protector device 10. For example, adjustable clamping joint 24 on the end of arm member 22 can be clamped to a clamp location 16 on outer flange portion 12. An opposite end of arm member 22 can be clamped to a rigid structure such as a base 40. In some cases, base 40 can be an operating table, or another suitably rigid structure. In some cases, a location on the body of the patient can serve as base 24.

In some cases, adjustable clamping joint 24 can have the ability to switch between a loosened configuration and a tightened configuration. In the loosened configuration, arm members 22 can be positionally adjusted in relation to outer flange portion 12, base 40, or another arm member 22. In the tightened configuration, arm members can be substantially rigidly coupled to outer flange portion 12, base 40, or another arm member 22 so as to resist movements between them. In some cases, two or more arm members 22 can be coupled together using adjustable clamping joint 24. In such cases, two or more arm members 22 coupled together can provide enhanced arm configuration adaptability.

The following actions may be included in the set-up of penile scaffold system 100. Clamping joints 24 can be in the loosened or substantially loosened configuration, i.e., so that clamping joints 24 can be manually adjusted. Insertable urethral protector device 10 can be engaged with penis 30. For example, elongate shank portion 14 can be inserted in the urethra of penis 30, and attachment devices 18 can be attached to the outer parts of penis 30. Clamping joints 24 on one end of arm members 22 can be coupled to clamp locations 16 on outer flange portion 12 of insertable urethral protector device 10. Clamping joints 24 on another end of arm members 22 can be coupled to one or more bases 40. Arm members 22 and insertable urethral protector device 10 can be positioned for the surgery as desired by the physician. Clamping joints 24 can be tightened to the tightened configuration. At this stage, set-up of penile scaffold system 100 can be complete so as to stabilize the penile anatomy for improved positional consistency, predictability, and stability during a surgery.

Figure 2:
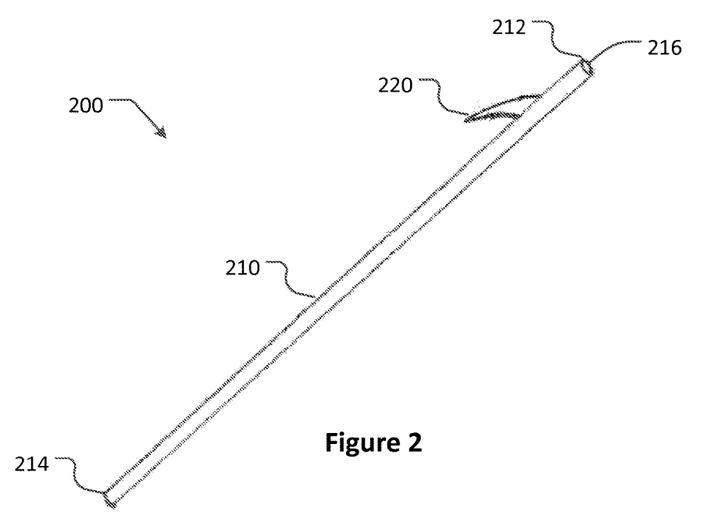
FIG. 2 is a diagram of a fibrotic tissue removal device in accordance with some embodiments provided herein.

In reference to FIG. 2, a fibrotic tissue removal device 200 in accordance with some embodiments can include a tube 210 and a blade 220. Tube 210 can include a distal end 212, a proximal end 214, and a lumen 216. In some cases, fibrotic tissue removal device 200 can be comprised of stainless steel. In some cases, fibrotic tissue removal device 200 can be comprised of a polymeric material. In some cases, blade 220 can be welded or glued to tube 210, and can include sharpened edges for severing fibrotic tissue. In some cases, two or more blades 220 can be attached to tube 210.

In some cases, fibrotic tissue removal device 200 can be long enough to reach to the distal end of the corpora cavernosa while extending proximally out of the corpora cavernosa far enough so that distal end 212 can be manipulated by a physician. For example, the length of fibrotic tissue removal device 200 can be about 120 to about 280 mm, about 140 to about 260 mm, about 160 to about 240 mm, or about 180 to about 220 mm.

In some cases, radiopaque markers can be included on certain locations of fibrotic tissue removal device 200. For example, such radiopaque markers can be placed on fibrotic tissue removal device 200 to indicate the location of blade 220.

In some cases, fibrotic tissue removal device 200 can be used over an implanted guidewire. For example, a guidewire can be positioned in a corpora cavernosa that contains fibrotic tissue. In such cases, fibrotic tissue removal device 200 can be installed over the guidewire, i.e., lumen 216 can be positioned to surround the guidewire, and fibrotic tissue removal device 200 can be advanced into the corpora cavernosa. The guidewire can direct the location of fibrotic tissue removal device 200 within the corpora cavernosa, and fibrotic tissue removal device 200 can be used to remove fibrotic tissue. For example, a physician can position blade 220 distal of the fibrotic tissue and then pull on distal end 214 to sever the fibrotic tissue by extracting or partially extracting fibrotic tissue removal device 200. In some cases, the severed fibrotic tissue can be removed from the corpora cavernosa in a suitable fashion.

In some cases, a cautery device can be used to remove fibrotic tissue from the corpora cavernosa. In some cases, a cautery device can be inserted over a guidewire as described above regarding fibrotic tissue removal device 200. In some cases, the cautery device can be an expandable balloon cautery device with a bi-polar cautery region on the distal tip of the balloon device.

Figure 3:
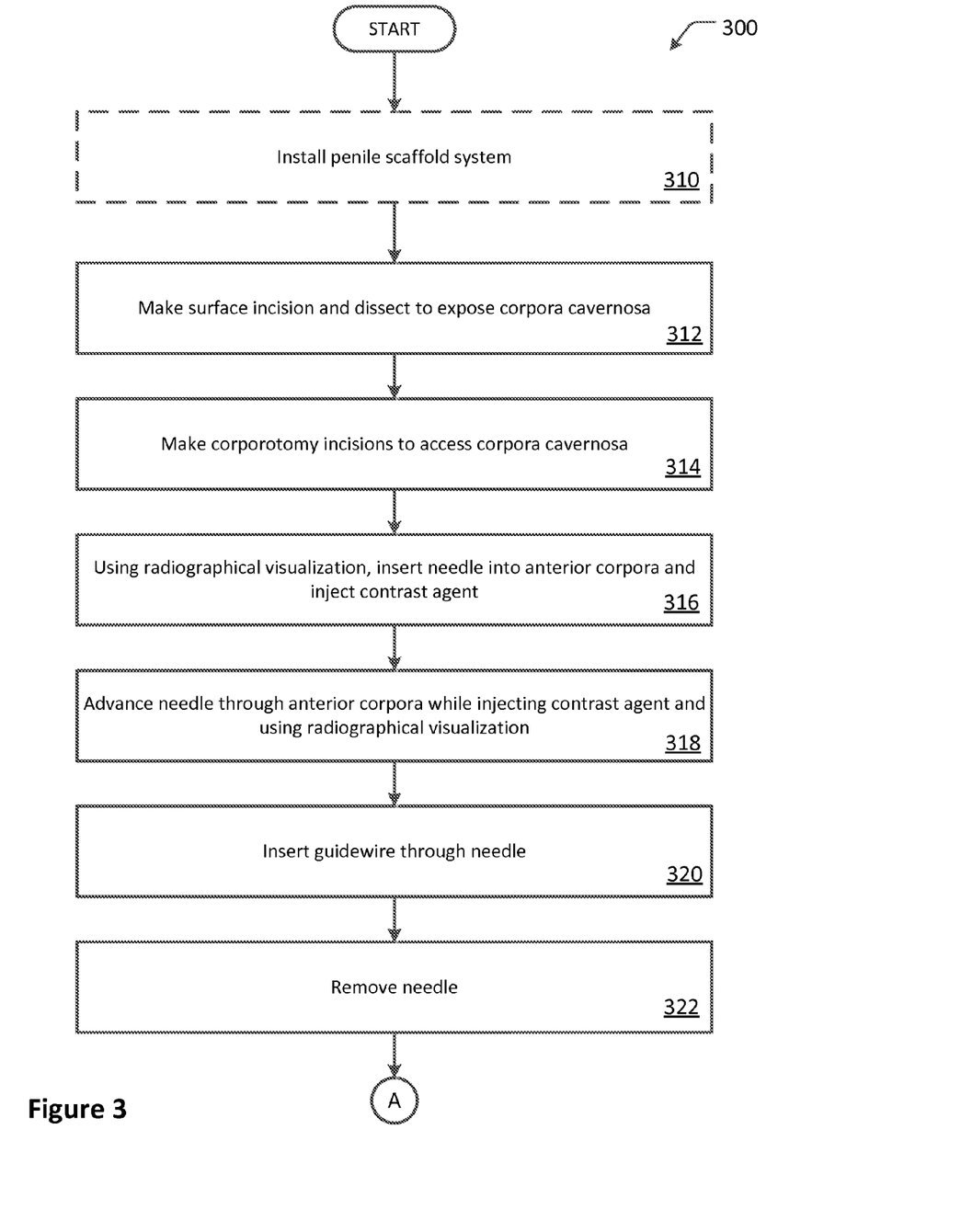
FIG. 3 is a flowchart of a method for penile prosthesis implantation surgery in accordance with some embodiments provided herein.

With reference to FIG. 3, a penile prosthesis implantation process 300 in accordance with some embodiments provided herein is illustrated. In general, process 300 includes radiographically-guided needle insertion into the corpora cavernosa, dilation of the corpora cavernosa, and insertion of penile implants. Process 300 can include implantation of prostheses in two corpora cavernosa. Therefore, as one of ordinary skill in the art will recognize, some steps of process 300 may be required to be repeated to complete the entire penile prosthesis implantation process 300.

At operation 310, a penile scaffold system can be optionally installed to stabilize the anatomy of the patient. The penile scaffold system used can be, for example, the penile scaffold system 100 as described in reference to FIG. 1.

At operation 312, an incision can be made, and tissue dissected, to gain access to the corpora cavernosa. In some cases, the incision can be an infrapubic incision. In some cases, the incision can be a penoscrotal incision, or any other suitable incision technique.

At operation 314, corporotomy incisions can be made to access the corpora cavernosa tissue. In some cases, the corporotomy incisions can be made at a location such that an anterior corpora cavernosa is defined, and a posterior corpora cavernosa is defined.

At operations 316 and 318, a physician can insert a needle a short distance into the anterior corpora cavernosa, and then inject a small amount of contrast agent. The physician can then view the contrast agent using an imaging system, e.g., a fluoroscopy system, or any other suitable imaging system. The imaging system can be used to determine the location of the needle tip in relation to the corpora cavernosa. In general, it may be desirable for the needle to be located at the approximate central axis of the corpora cavernosa. Using the imaging system, the physician can make adjustments to the location of the needle accordingly. Operation 316 continues by the physician making further advancements of the needle, while injecting more contrast agent. The contrast agent makes the position of the needle with respect to the corpora cavernosa visible via the imaging system as the physician advances the needle. In this fashion, operation 316 facilitates the accurate placement of a needle near the axial centerline, or other desired position, within the corpora cavernosa. The distal tip of the needle can be advanced toward the distal end of the corpora cavernosa. In some cases, the needle can include distance indicators to use for sizing the implant to be used in the anterior corpora cavernosa.

The image-guided approach described herein can also facilitate the deployment of multiple miniature rods (polymer or metallic based). Such miniature rods when configured in a geometric design may function as a non-inflatable penile prosthesis.

The image-guided approach described herein can also facilitate the delivery of other treatments for erectile dysfunction. For example, the image-guided techniques described herein can be used to deliver tissue engineered cells and growth factors to treat erectile dysfunction.

At operation 320, a guidewire can be inserted through the lumen of the needle. At operation 322, the needle can be removed from the anterior corpora cavernosa. The guidewire can remain within the anterior corpora cavernosa.

At operation 324, the needle can be optionally inserted into the posterior corpora cavernosa. Again, a contrast dye can be injected, and an imaging system can be used to verify accurate placement of the needle as desired within the posterior corpora cavernosa.

At operation 326, a dilator can be installed over the guidewire located in the anterior corpora cavernosa. The dilator can include a central lumen through which the guidewire is located. In some cases, the dilator can be a blunt instrument or a series of progressively larger blunt instruments. In some cases, the dilator can be a balloon dilator. The balloon dilator can be inserted in a low profile configuration, which may potentially allow for a smaller corporotomy incision. After placement within the corpora cavernosa, the balloon dilator can be expanded to perform the dilation. In some cases, the dilator can include distance indicators to use for sizing the implant to be used in the anterior corpora cavernosa. In some cases, at the completion of operation 326, the corpora cavernosa can be dilated, but the presence of fibrotic tissue may to some extent prevent complete dilation as desired.

At operation 328, cutting devices are optionally used to remove fibrotic corporal tissue as needed. In some cases, a mechanical cutting device such as fibrotic tissue removal device 200 can be used. In some cases, a cautery cutting device can be used, such as a balloon cautery device. In some cases, the cutting devices can be installed over the guidewire.

At operation 330, the posterior corpora cavernosa is dilated. If optional step 324 was used, the guidewire can be used to direct the dilator as in operation 326. In some cases, dilatation of the posterior corpora cavernosa based on tactile feedback and without usage of a guidewire can be performed.

At operation 332, penile prosthesis cylinders are implanted over the guidewire(s). To facilitate this approach, penile prosthesis cylinders have a central lumen to permit insertion over a guidewire as described below in reference to FIG. 4. In some cases, the penile prosthesis cylinders can be contained within sheaths. In some cases, the sheath can be used temporarily to assist with the insertion process, and then removed when the penile prosthesis cylinders are located properly within the corpora cavernosa. In some cases, the sheath can comprise a biosorbable material. In such cases, the sheath can remain on the penile prosthesis cylinders after the implantation surgery until the biosorbtion process occurs. In some cases, the sheath can remain on the penile prosthesis cylinders indefinitely, and can function to reinforce a weakened tunica albuginea. In such cases, the sheath can be resilient and expandable to be compatible with the expansion of the penile prosthesis cylinders. In some cases, the sheath can include an antibiotic coating. In such cases, such an antibiotic coating can prevent or reduce the risk of infections, reduce the potential for scarring, and enhance healing.

At operation 334, in some cases, the implants can optionally be a two-part design with the two parts being physically conjoined in situ. That is, in some cases the anterior implant can be a physically separate item from the posterior implant. The separate implants can be separately installed, i.e. one implant can be installed in the anterior corpora cavernosa and the other implant can be installed in the posterior corpora cavernosa. With the implants so installed, the implants can then be coupled together in situ to make them a unitary implant. For example, in some cases, the anterior cylinder can be coupled to the posterior cylinder using a threaded coupling. In some cases, a biocompatible adhesive can be used to couple the anterior and posterior cylinders. In some cases, a magnetic coupling can be used to couple the anterior and posterior cylinders. In some cases, a mechanical compression coupling can be used to couple the anterior and posterior cylinders. In some cases, other suitable methods for coupling the anterior and posterior cylinders in situ can be used.

At operation 336, the guidewires can be removed from the corpora cavernosa. At this stage, the implantation of the penile prosthesis cylinders according to process 300 is complete, and the surgery can be concluded in the typical fashion.

In some cases, an image-guided approach provided herein can facilitate the deployment of multiple miniature rods that can be polymeric or metallic based. Such miniature rods when configured in a geometric design may function as a non-inflatable penile prosthesis.

In some cases, an image-guided approach provided herein can facilitate the delivery of other treatments for erectile dysfunction. For example, an image-guided technique provided herein can be used to deliver tissue engineered cells and growth factors to treat erectile dysfunction.

Figure 4:
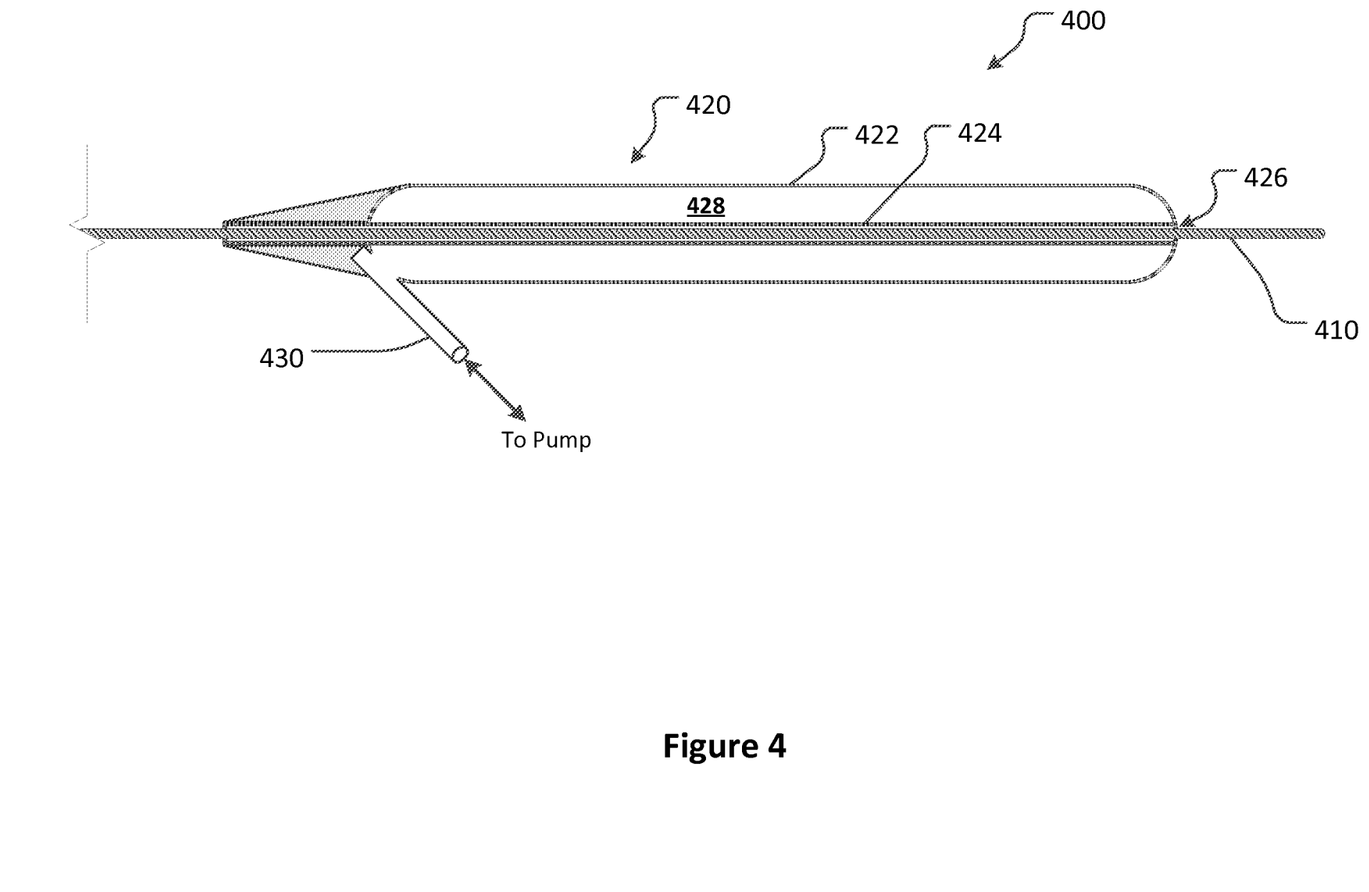
FIG. 4 is a schematic cross-section of a penile prosthesis with a central lumen in accordance with some embodiments provided herein.

With reference to FIG. 4, an exemplary penile prosthesis system 400 is illustrated in an axial cross-sectional view. Prosthesis system 400 includes a penile prosthesis 420 and a guidewire 410.

Prosthesis 420 can include a central lumen 426 that surrounds or partially surrounds guidewire 410. In some cases, guidewire 410 can be used to direct implantation of prosthesis 420 (e.g., as in penile prosthesis implantation process 300 described herein). In some cases, prosthesis 400 can be an over-the-wire penile prosthesis. After implantation of prosthesis 400, guidewire 410 can be removed, leaving prosthesis 400 implanted within a penis in a desired location as directed by guidewire 410.

Prosthesis 400 can be an inflatable cylinder. A chamber 428 can be defined by an outer wall 422 and an inner wall 424. Inner wall 424 can define lumen 426. Chamber 428 can be filled with a fluid, such as saline, to enlarge prosthesis 400 to simulate a penile erection. Chamber 428 can be filled and emptied via a tube 430. One end of tube 430 can be in fluid communication with chamber 428, and the other end of tube 430 can be in fluid communication with a typical penile prosthesis system pump (not shown).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described devices and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for implanting a penile prosthesis, wherein said method comprises:
    (a) inserting a needle into a corpora cavernosa of a male human;
    (b) injecting, via said needle, contrast dye into said corpora cavernosa;
    (c) observing, using radiography, a position of said needle in relation to said corpora cavernosa;
    (d) directing, in response to said observing, said needle to a desired position in relation to said corpora cavernosa;
    (e) inserting a guidewire through a lumen of said needle;
    (f) removing said needle from said corpora cavernosa;
    (g) inserting, over said guidewire, a dilator into said corpora cavernosa;
    (h) dilating said corpora cavernosa;
    (i) inserting, over said guidewire, a penile implant into said corpora cavernosa; and
    (j) removing said guidewire.

2. The method of claim 1, wherein said method comprises installing a penile stabilization device to a penis of said male human.

3. The method of claim 1, wherein said method comprises removing fibrotic tissue from said corpora cavernosa.

4. The method of claim 1, wherein inserting said penile implant comprises:
    (a) inserting an anterior penile implant into an anterior portion of said corpora cavernosa;
    (b) inserting a posterior penile implant into a posterior portion of said corpora cavernosa; and
    (c) coupling said anterior penile implant to said posterior penile implant, wherein said coupling is performed with said anterior penile implant being at least partially within said anterior portion of said corpora cavernosa and with said posterior penile implant being at least partially within said posterior portion of said corpora cavernosa.

5. A system for implanting a penile prosthesis, wherein said system comprises:
    (a) a needle with a lumen, wherein said needle is configured to inject a contrast dye into a corpora cavernosa;
    (b) a radiography system configured to display an image of said contrast dye within said corpora cavernosa;
    (c) a guidewire configured to be inserted through said lumen of said needle and configured to be inserted into said corpora cavernosa;
    (d) a dilator defining a dilator lumen that configures said dilator to be installed into said corpora cavernosa over said guidewire; and
    (e) a penile prosthesis defining a prosthesis lumen therethrough that configures said penile prosthesis to be installed into said corpora cavernosa over said guidewire.

6. The system of claim 5, wherein said system comprises a penile stabilization device.

7. The system of claim 6, wherein the penile stabilization device comprises:
(a) a urethral protector, comprising an elongate element configured to be inserted into a urethra of a penis, an outer portion coupled to said elongate element and configured to be attached to an outer surface of said penis;
(b) one or more arm members, comprising a first end configured to be coupled to said outer portion of said urethral protector and a second end configured to be coupled to a base; and
(c) one or more clamping joints, wherein said clamping joints are configured to switch between a loosened configuration and a tightened configuration, wherein in said loosened configuration said penile stabilization device is flexibly movable, and wherein in said tightened configuration said penile stabilization device is rigidly fixed in a position.

8. The system of claim 5, wherein said system comprises a device configured for severing fibrotic tissue from within said corpora cavernosa.

9. The system of claim 8, wherein said device configured for severing fibrotic tissue comprises a blade configured to shear said fibrotic tissue, and wherein said device comprises a lumen configured for installation over said guidewire.

10. The system of claim 8, wherein said device configured for severing fibrotic tissue comprises a balloon with a bi-polar electro-cautery portion on a distal tip of said balloon, and wherein said balloon is configured for installation over said guidewire.

11. The system of claim 5, wherein said penile prosthesis comprises an inflatable penile prosthesis.

12. An inflatable penile prosthesis device defining a central lumen therethrough, wherein the central lumen is arranged to releasably receive a guidewire such that the inflatable penile prosthesis is guidable during implantation into a penis using an over-the-wire technique.

13. The inflatable penile prosthesis device of claim 12, wherein the inflatable penile prosthesis device is inflatable.

14. The inflatable penile prosthesis device of claim 12, wherein the inflatable penile prosthesis device comprises a chamber that surrounds the central lumen and that is configured to receive a fluid for inflating the inflatable penile prosthesis device.

15. The inflatable penile prosthesis device of claim 14, wherein the inflatable penile prosthesis device further comprises a tube in fluid communication with the chamber, and wherein the tube is configured for connecting the inflatable penile prosthesis device with a pump.

16. The inflatable penile prosthesis device of claim 12, wherein the central lumen extends along a longitudinal axis of the inflatable penile prosthesis device.

\* \* \* \* \*